United States Patent
Bingham (10) Patent No.: US 10,010,309 B2
(45) Date of Patent: Jul. 3, 2018

(54) SURGICAL DEVICE WITH OVERLOAD MECHANISM

(71) Applicant: Ethicon LLC, Guaynabo, PR (US)

(72) Inventor: Scott R. Bingham, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 644 days.

(21) Appl. No.: 14/511,681

(22) Filed: Oct. 10, 2014

(65) Prior Publication Data

US 2016/0100902 A1  Apr. 14, 2016

(51) Int. Cl.
| | |
|---|---|
| *A61B 17/00* | (2006.01) |
| *A61B 17/28* | (2006.01) |
| *A61B 17/29* | (2006.01) |
| *A61B 17/072* | (2006.01) |
| *A61B 90/00* | (2016.01) |

(52) U.S. Cl.
CPC ............ *A61B 17/00* (2013.01); *A61B 17/072* (2013.01); *A61B 17/07207* (2013.01); *A61B 17/2841* (2013.01); *A61B 17/2909* (2013.01); *A61B 90/03* (2016.02); *A61B 2017/2925* (2013.01); *A61B 2090/065* (2016.02)

(58) Field of Classification Search
CPC ..... A61B 17/00; A61B 90/03; A61B 17/2841; A61B 17/072; A61B 17/07207; A61B 17/2909; A61B 2090/065
See application file for complete search history.

(56) References Cited

U.S. PATENT DOCUMENTS

| | | | |
|---|---|---|---|
| 5,190,541 A | 3/1993 | Abele et al. | |
| 5,445,638 A | 8/1995 | Rydell et al. | |
| 5,976,160 A * | 11/1999 | Crainich ............ | A61B 17/2909 606/142 |
| 6,071,299 A | 6/2000 | Dingler et al. | |

(Continued)

FOREIGN PATENT DOCUMENTS

| | | |
|---|---|---|
| DE | 29806799 U1 | 6/1998 |
| EP | 1712188 A2 | 10/2006 |

(Continued)

OTHER PUBLICATIONS

International Search Report for Application No. PCT/US2015/053108 dated Feb. 1, 2016 (4 pages).

*Primary Examiner* — Richard Louis
(74) *Attorney, Agent, or Firm* — Mintz Levin Cohn Ferris Glovsky and Popeo, P.C.

(57) ABSTRACT

Methods and devices are provided for preventing surgical devices used in laparoscopic procedures including opposed jaws and an overload mechanism from overloading the opposed jaws of the device. In one embodiment a surgical device, includes a handle and an elongate shaft extending distally therefrom with opposed jaws coupled to a distal end thereof. The surgical device can include a trigger pivotally movable about a first pivot axis during a first range of motion from an open position toward a closed position, to cause the opposed jaws of the end effector to move from an open position to a partially closed position. The trigger can further be pivotally movable about a second pivot axis during a second range of motion from the partially closed position to the fully closed position, without causing corresponding movement of the opposed jaws from the open position to the closed position.

18 Claims, 9 Drawing Sheets

(56) References Cited

U.S. PATENT DOCUMENTS

| | | |
|---|---|---|
| 6,500,176 B1 | 12/2002 | Truckai et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 2011/0087218 A1* | 4/2011 | Boudreaux ........ A61B 18/1445 606/41 |
| 2012/0078243 A1 | 3/2012 | Worrell et al. |
| 2012/0078247 A1 | 3/2012 | Worrell et al. |
| 2012/0083783 A1 | 4/2012 | Davison et al. |
| 2012/0184990 A1* | 7/2012 | Twomey ............ A61B 17/2909 606/206 |
| 2012/0207309 A1 | 8/2012 | Eppolito |

FOREIGN PATENT DOCUMENTS

| | | |
|---|---|---|
| WO | 97010764 A1 | 3/1997 |
| WO | 00024330 A1 | 5/2000 |
| WO | 00024331 A1 | 5/2000 |

\* cited by examiner

SURGICAL DEVICE WITH OVERLOAD MECHANISM

FIELD OF THE INVENTION

The present invention relates to surgical devices having an overload mechanism for preventing overload of a force applied to close the opposed jaws on an end effector of the device, as well as to methods for preventing overload on a surgical device.

BACKGROUND OF THE INVENTION

In recent years surgery has markedly advanced through the performance of laparoscopic and endoscopic surgical procedures such as cholecystectomies, gastrostomies, appendectomies, and hernia repair. Laparoscopic surgery, which can also be referred to as minimally invasive surgery, is a surgical technique that includes operations performed through small incisions in the body of a patient. There can be a number of advantages to the patient with laparoscopic surgery compared to open procedures where larger incisions are made. For example, pain and hemorrhaging can be reduced due to the smaller incisions and recovery times can be shorter.

In a conventional laparoscopic procedure, a distal end of a laparoscopic or electrosurgical device can be passed through a small incision in the skin of a patient. The distal end of the laparoscopic device is then positioned at or adjacent a surgical site. One or more surgical procedures are then performed at the surgical site, which can include cutting and/or sealing tissue. The distal end of the laparoscopic device can be removed from the patient after the completion of the surgical procedure.

Many laparoscopic devices include a pair of jaws for grasping or otherwise effecting tissue. Movement of the jaws between open and closed positions is controlled by an actuation assembly, which transmits a force from the handle to the opposed jaws. The force required to close the jaws can increase with thicker or stiffer tissue, and/or in applications where the jaws are applying a closure mechanism, such as a clip or staple, to the tissue. In the event that excessive forces are transmitted by the actuation assembly, undesired damage to the tissue can result. In addition, since the actuation assembly requires precise timing and coordinated movement between numerous components, excessive forces applied to close the jaws can result in damage to the components of the actuation assembly.

Accordingly, there remains a need for improved methods and devices for preventing overload of a force applied to close opposed jaws on a surgical end effector.

SUMMARY OF THE INVENTION

The present invention generally provides methods and devices for preventing overload on opposed jaws of surgical devices used in laparoscopic surgery. In one embodiment, a surgical device for stapling tissue is provided and includes a handle and an elongate shaft extending distally therefrom with opposed jaws coupled to a distal end thereof. The surgical device can further include a trigger coupled to the handle and movable between an open position and a closed position. The trigger can be pivotally movable about a first pivot axis during a first range of motion from the open position toward the closed position to cause the opposed jaws of the end effector to move from an open position to a partially closed position. The trigger can further be pivotally movable about a second pivot axis during a second range of motion, from the partially closed position to the fully closed position. The jaws can be configured to remain stationary during movement of the trigger.

In some embodiments, the device can include an overload mechanism disposed within the handle, and the trigger can be configured to apply a force to the overload mechanism during movement about the second pivot point. The trigger can also include a pin mounted thereon and coupled to the overload mechanism. The pin can remain stationary during movement of the trigger about the first pivot axis and the pin can slide within the overload mechanism during movement of the trigger about the second pivot point. In certain embodiments, the overload mechanism can include a carriage that receives the pin on the trigger, and a biasing element that applies a proximal biasing force to the carriage. The pin can cause distal movement of the carriage during movement of the trigger about the second pivot point.

In some embodiments, the device can include an actuation assembly disposed within the housing and the elongate shaft and coupled between the trigger and the opposed jaws. Movement of the trigger about the first pivot axis can be effective to advance the actuation assembly through the elongate shaft, causing the opposed jaws to move from the open position to the partially-closed position. The actuation assembly can also include a cam lever coupled between the trigger and the actuation assembly. The trigger can cause pivotal movement of the cam lever about a third pivot axis during movement of the trigger about the first pivot point, such that the cam lever applies a force to advance the actuation assembly through the elongate shaft.

In other aspects, an overload mechanism disposed within the handle housing can apply a biasing force to the trigger. The biasing force can prevent movement of the trigger about the second pivot axis until a force to pivot the trigger exceeds a threshold force of the biasing mechanism.

In another embodiment, a surgical device is provided having a handle housing with a trigger coupled thereto. The surgical device can also include an elongate shaft extending distally from the handle housing. The elongate shaft can have an end effector with opposed jaws coupled to a distal end thereof. The surgical device can further include an actuation assembly extending through the handle housing and the elongate shaft and configured to actuate the end effector. The surgical device can also include a cam lever disposed within the handle housing and coupled between the trigger and the actuation assembly. Movement of the trigger can cause the cam lever to pivot which in turn advances the actuation assembly to actuate the end effector. The surgical device can further include an overload mechanism disposed within the handle housing and configured to apply a proximal biasing force to the trigger to maintain the trigger in a first position. In the first position, movement of the trigger is effective to cause the cam lever to pivot and thereby advance the actuation assembly to actuate the end effector. When a force applied to the trigger exceeds a predetermined threshold force of the overload mechanism, the overload mechanism allows the trigger to move to a second position. The overload mechanism can allow the trigger to continue to pivot without causing further pivotal movement of the cam lever. In some embodiments, the actuation assembly can be effective to close the opposed jaws of the end effector.

In certain embodiments, the overload mechanism can include a biasing element that applies the biasing force to the trigger. For example, the overload mechanism can include a housing can have a biasing element biasing a carriage disposed within the housing, and the trigger having a pin that can be received within the carriage. The biasing element can bias the carriage in a proximal direction, and movement of the trigger about the second pivot axis can causes the carriage to move distally within the housing.

In some embodiments, the surgical device can have the overload mechanism positioned distal of the cam lever. In certain aspects of the invention, the surgical device can further include a pin coupled between the trigger and the cam lever such that rotation of the trigger causes rotation of the cam lever. In some embodiments, the cam lever is disposed about a third pivot point. The trigger can pivot in the first position to cause the cam lever to pivot about the third pivot point. The cam lever can remain stationary about the third pivot axis during movement of the trigger in the second position.

In other aspects, the pin on the trigger can apply a force to the cam lever to cause pivotal movement the cam lever when the trigger moves in the first position. The trigger can pivot about a first pivot axis in the first position, and the trigger can pivot about a second pivot axis in the second position.

In some embodiments, a method of operating a surgical device is provided. The method can include actuating a trigger movably coupled to a handle housing to cause the trigger to pivot about a first pivot axis and thereby advance an actuation assembly extending through an elongated shaft extending distally from the handle assembly. Advancement of the actuation assembly cause opposed jaws at a distal end of the elongate shaft to move from an open position to a closed position. An overload mechanism disposed within the handle housing can allow the trigger to pivot about a second pivot axis when a force applied to the trigger to close the opposed jaws exceeds a predetermined level without further advancing the actuation assembly to close the opposed jaws.

In other aspects, the method can include movement of the trigger about the second pivot point, causing a pin on the trigger to slide distally within the overload mechanism to overcome a biasing force of a biasing element disposed within the overload mechanism.

In other aspects, the method can include movement of the trigger about the first pivot point, causing pivotal movement of a cam lever within the housing. The cam lever can cause advancement of the actuation assembly and the cam lever remains stationary during movement of the trigger about the second pivot point.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute In general, methods and devices are provided for preventing overload on a surgical device having opposed jaws. In general, a surgical device is provided having a handle and an elongate shaft extending distally therefrom with opposed jaws coupled to a distal end. A trigger is coupled to the handle and movable between an open position and a closed position for causing corresponding movement of the jaws between open and closed positions. The device can further include an overload mechanism that prevents an excessive closure force from being applied to the jaws when resistance is encounter. The overload mechanism allows the trigger to continue to move toward the closed position without causing further movement of the opposed jaws.

A person skilled in the art will appreciate that the overload devices and methods disclosed herein can be used with a variety of surgical devices, including staplers, cutters, graspers, clip appliers, suturing devices, etc., and it can be used to prevent overload on a variety of actuation mechanisms, including mechanisms for opening and closing jaws, firing staples or clips, articulating an end effector, etc. Exemplary devices are disclosed, by way of non-limiting example, in the following patents and publications, which are incorporated by reference in their entireties herein: U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218; U.S. Pub. No. 2012/0207309A1; U.S. Pub. No. 2012/0078247A1; U.S. Pub. No. 2012/0083783A1, and U.S. Pub. No. 2012/078243A1.

Figure 1A:
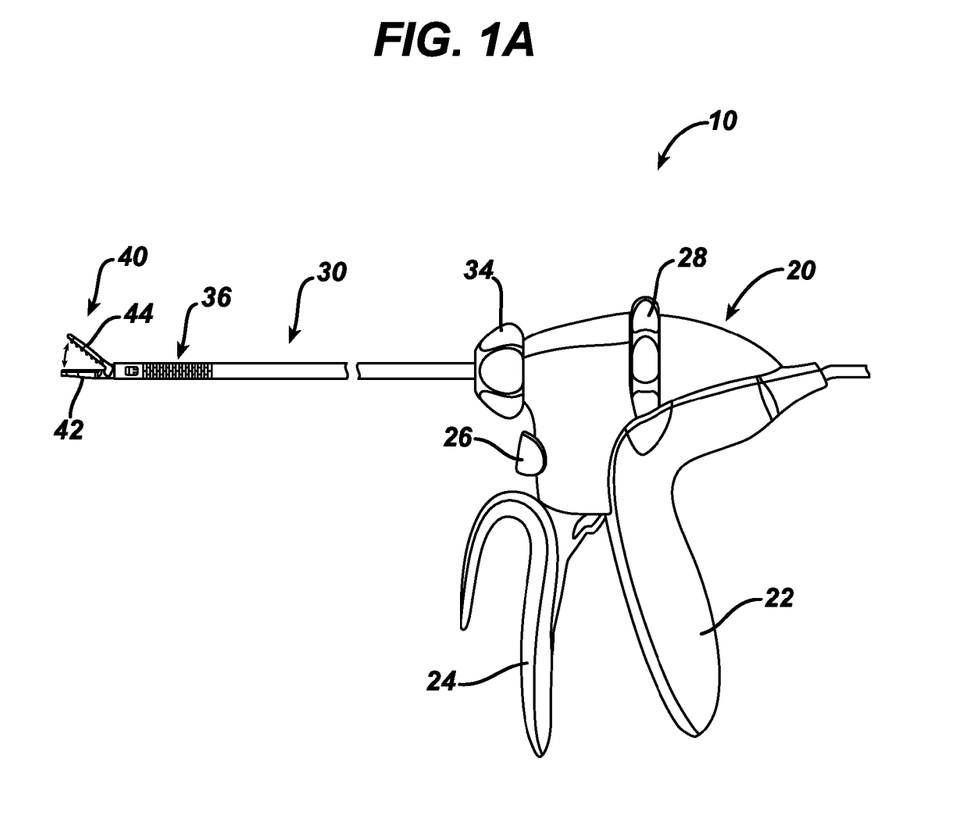
FIG. 1A is a perspective view of one embodiment of a surgical instrument having a handle assembly and an elongate shaft extending therefrom.

FIG. 1A shows one embodiment of an electrosurgical device or instrument 10 that is constructed and operable in accordance with at least some of the teachings of the above referenced patents and publications. The illustrated electrosurgical instrument 10 includes a handpiece 20, an elongated shaft 30 extending distally from handpiece 20, and an end effector 40 disposed at a distal end of shaft 30. The handpiece 20 in the illustrated embodiment has a pistol grip configuration, with a stationary handle 22 and a moveable handle or trigger 24. A person skilled in the art will appreciate that the handpiece can have a variety of configurations other than pistol-grip, including, for example, a scissor grip, or any other grip known in the art. As further shown in FIG. 1A, the device includes an activation button 26, and an articulation control 28. The end effector 40 can also have various configurations, but in the illustrated embodiments the end effector 40 includes a first jaw 42 and a second jaw 44. The opposed jaws 42, 44 may be operably coupled together such that the one or both jaws can move between an open position and a closed position for grasping tissue.

In use, the trigger 24 is pivotable toward and away from the stationary handle 22 to selectively open and close the opposed jaws 42, 44 of the end effector 40. The activation button 26 is operable to selectively activate RF circuitry that is in communication with the end effector 40, as will also be described in greater detail below. In some versions, the activation button 26 can also serve as a mechanical lockout against the trigger 24, such that the trigger 24 cannot be actuated unless the activation button 26 pressed simultaneously. Examples of how such a lockout may be provided are disclosed in one or more of the references cited herein. The articulation control 28 is operable to selectively control articulation of the end effector about an articulation joint 36. In some versions, the handpiece 20 can include a knob 34 for causing rotation of the shaft 30 about the longitudinal axis defined by elongate shaft 30. Such rotation may provide rotation of end effector 40 and shaft 30 unitarily. In other versions, the knob 34 can be operable to rotate the end effector 40 without rotating any portion of the shaft 30 that is proximal of articulation section 36. As another merely illustrative example, the electrosurgical instrument 10 can include one rotation control that provides rotatability of the shaft 30 and the end effector 40 as a single unit, and another rotation control that provides rotatability of the end effector 40 without rotating any portion of the shaft 30 that is proximal of articulation section 36. Other suitable rotation schemes will be apparent to those of ordinary skill in the art in view of the teachings herein. Of course, rotatable features may simply be omitted if desired.

Figure 1B:
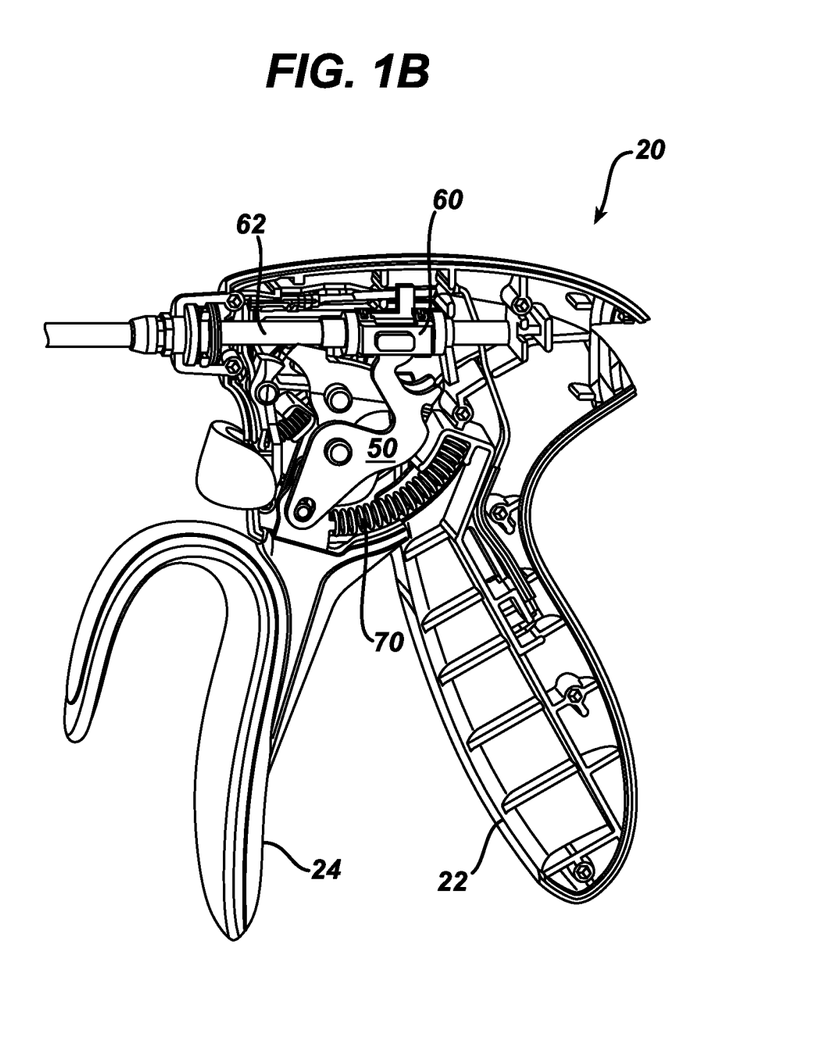
FIG. 1B is an internal perspective view of the surgical instrument of FIG. 1A, showing an actuation assembly having a trigger, a cam lever, and a sled.

FIG. 1B illustrates the internal components of the handpiece 20, and in particular the components of the actuation assembly that are effective to transfer a force from the trigger 24 to the jaws 42, 44 of the end effector 40. While the actuation assembly can have various configurations, in the illustrated embodiment the actuation assembly generally includes the trigger 24, a cam lever 50 coupled to the trigger 24, a sled 60 coupled to the cam lever 50, and an actuation shaft 62 coupled to the sled 60. In general, the trigger 24 is configured to move toward the stationary handle 22, which in turn causes the cam lever 50 to rotate and to thereby advance the sled 60 distally. In turn, the sled 60 causes distal movement of the actuation shaft 62 coupled thereto. While not shown, distal movement of the actuation shaft 62 is effective to cause the jaws 42, 44 of the end effector 40 to move from an open position to a closed position, as explained in the above referenced patents and publications.

Figure 2:
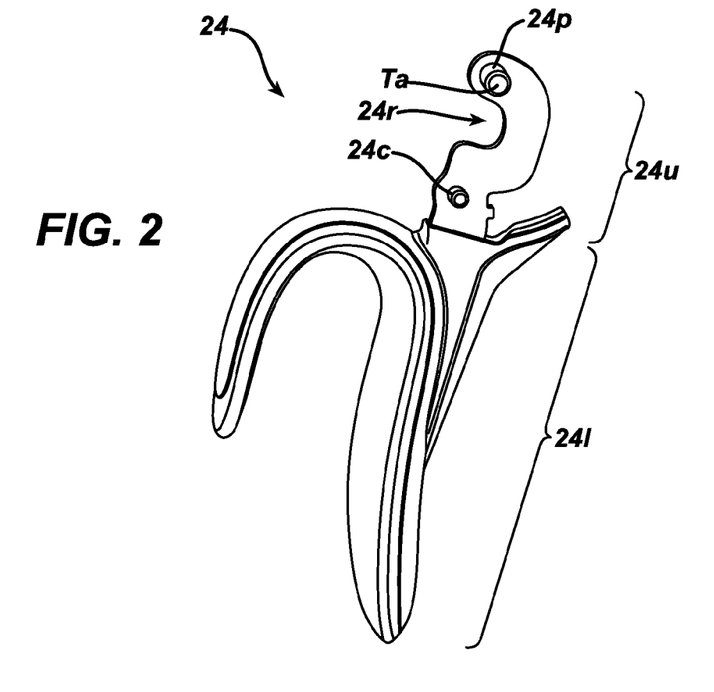
FIG. 2 is a side perspective view of the trigger of FIG. 1B.

FIG. 2 illustrates the trigger 24 in more detail. The shape of the trigger 24 can vary depending on the other components of the housing, but in the illustrated embodiment the trigger 24 generally includes an upper portion 24$u$ and a lower portion 24$l$. The lower portion 24$l$ can be configured to facilitate grasping by a user. As shown in FIG. 2, the lower portion 24$l$ is generally hook shaped to receive a user's fingers for pulling the trigger 24 toward the stationary handle 22, however the lower portion can have various other configurations. The upper portion 24$u$ is configured to be disposed within the handpiece and is configured to interact with the cam lever 50. In the illustrated embodiment, the upper portion 24$u$ has a backwards substantially C-shaped configuration with a 24$r$ formed therein for facilitating movement of the trigger 24, as will be discussed below. As further shown in FIG. 2, the upper portion 24$u$ includes a trigger pivot pin 24$p$ and a trigger camming pin 24$c$, each of which can extend through bores formed in the upper portion 24$u$ or can be integrally formed on the upper portion 24$u$. The trigger pivot pin 24$p$ defines a trigger pivot axis $T_a$ about which the trigger 24 can rotate under normal load conditions. When the trigger 24 is coupled to the hand piece, the trigger pivot pin 24$p$ will be mounted within the handpiece 20 to allow pivotal movement of the trigger 24 about the first pivot axis $T_a$. As will be discussed in more detail below, in one exemplary embodiment the trigger pivot pin 24$p$ can be disposed within an overload mechanism such that the trigger pivot pin 24$p$ is allowed to move within the handpiece 20 when an overload force is encountered. The trigger camming pin 24$c$, on the other hand, is configured to act upon the cam lever 50 during pivotal movement of the trigger 24 about the trigger pivot axis $T_a$. In particular, when the trigger 24 is pivoted in a counterclockwise direction about the trigger pivot axis $T_a$, i.e., toward the stationary handle 22, the trigger camming pin 24$c$ will contact and apply a force to the cam lever 50 to cause pivotal movement of the cam lever 50, as explained below.

Figure 3:
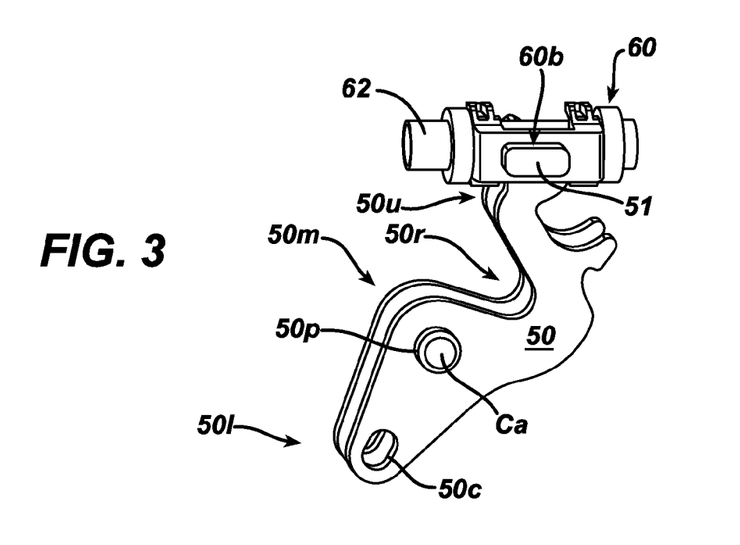
FIG. 3 is a side perspective view of the cam lever and sled of FIG. 1B.

FIG. 3 illustrates the cam lever 50 and the sled 60 in more detail. The cam lever 50 generally includes a lower portion 50$l$ that is coupled to the trigger camming pin 24$c$ on the trigger 24, a mid-portion 50$m$ having a cam lever pivot pin 50p extending through a bore formed therein or integrally formed thereon, and an upper portion 50u that is coupled to the sled 60. A person skilled in the art will appreciate that the cam lever 50 can be in the form of a single plate, or two parallel plates as shown. The cam lever pivot pin 50p at the mid-portion 50m of the cam lever 50 defines a fixed cam lever pivot axis $C_a$ about which the cam lever 50 can rotate. The cam lever pivot pin 50p can thus be fixedly mounted within the handpiece 20, e.g., disposed within receiving portions formed in shrouds of the handpiece 20 or otherwise held stationary within the handpiece 20. When disposed within the handpiece 20, the cam lever pivot pin 50p can be positioned adjacent to the recess 24r formed in the distal-facing surface of the trigger 24.

The lower portion 50l of the cam lever 50 can include a camming bore 50c formed therein that receives the trigger camming pin 24c on the trigger 24. A person skilled in the art will appreciate that the cam lever 50 can conversely have a pin formed thereon that extends through a bore formed in the trigger 24. In either configuration, the coupling will allow the two components to move in coordination, while still allowing free rotation of the pin within the bore so as to allow the trigger 24 and the cam lever 50 to pivot about their respective different pivot axes $T_a$, $C_a$.

The upper portion 50u can be coupled to the sled 60 using various techniques, but as shown the upper portion 50u includes protrusions (only one protrusion 51 is shown) formed thereon that are received within bores 60b formed in the sled 60. Furthermore, the upper portion 50u of the cam lever 50 can include a recess 50r formed in a distal facing surface. The recess 50r can be configured to receive the trigger pivot pin 24p when the cam lever 50 is rotated to cause distal movement of the sled 60.

Figure 4:
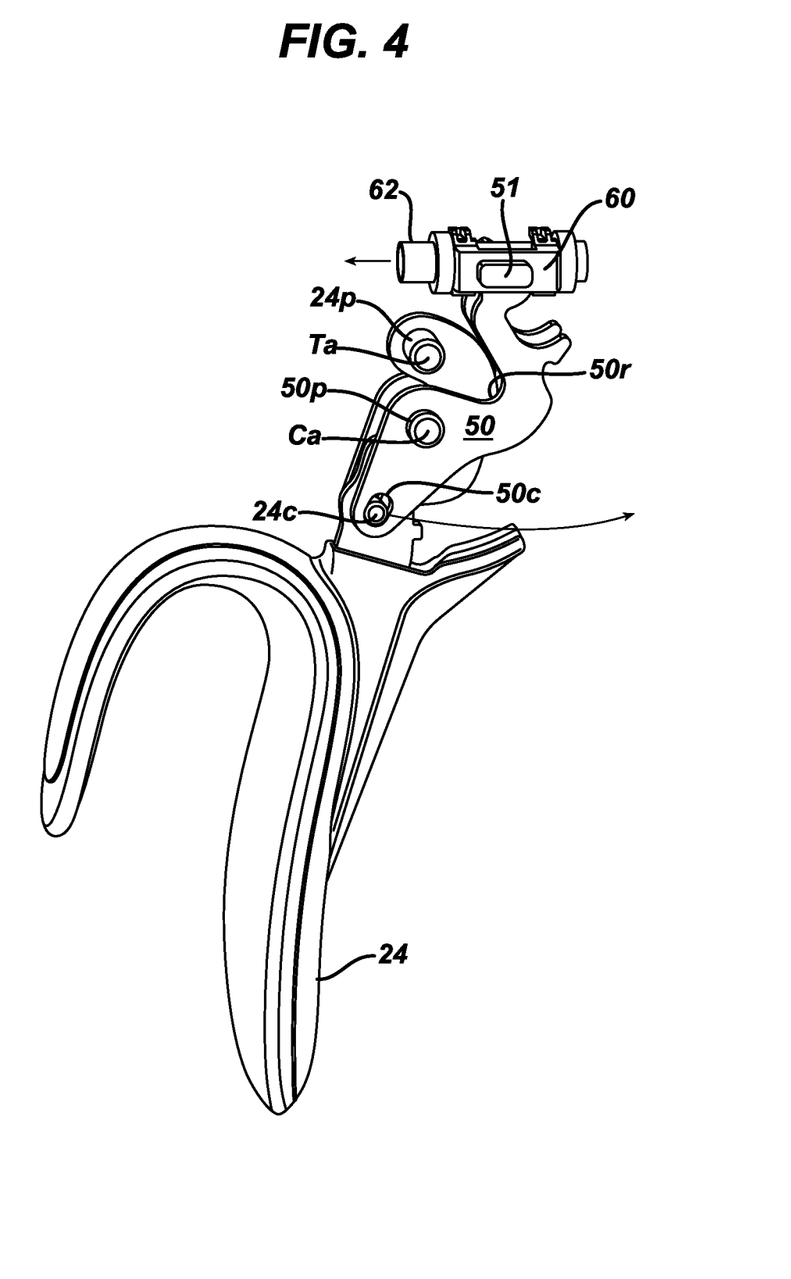
FIG. 4 is a side perspective view of the trigger, cam lever, and sled of FIG. 1B, shown in the assembled configuration.

FIG. 4 illustrates the trigger 24, cam lever 50, and sled 60 in the assembled configuration. In use, when the trigger 24 is rotated counterclockwise about the trigger pivot axis $T_a$, e.g., by moving the trigger 24 toward the stationary handle 22, the trigger camming pin 24c will move in a proximal direction along an arcuate path as indicated by the arrow. This movement of the trigger camming pin 24c will cause corresponding proximal movement of the camming bore 50c in the cam lever lower portion 50l, thereby causing the cam lever 50 to pivot counterclockwise about the cam lever pivot axis $C_a$ and causing the upper portion 50u of the cam lever 50 to move in a distal direction to cause distal movement of the sled 60 as indicated by the arrow. When the sled 60 is advanced distally, the jaws of the end effector will be moved from an open position toward a closed position. Full rotation of the trigger 24 about the trigger pivot axis $T_a$ will cause corresponding full closure of the jaws. Conversely, when the trigger 24 is released, i.e., moved away from the stationary handle 22, the trigger 24 will pivot in a clockwise direction about the trigger pivot pin 24p, which will cause the trigger camming pin 24c to move in a distal direction, thereby moving the lower portion 50l of the cam lever 50 distally and causing the cam lever 50 to pivot in a clockwise direction about the cam lever pivot axis $C_a$. The upper portion 50u of the cam lever will thus move in a proximal direction to move the sled 60 proximally and thereby cause the jaws to move to an open position. As shown in FIG. 1B, a biasing spring 70 can be provided to bias the trigger 24 to the illustrated initial position, spaced from the stationary handle 22, and a force can be applied to overcome the bias of the spring 70 and to move the trigger 24 to the actuated position, adjacent to the stationary handle 22. When the trigger 24 is released from the actuated position, the biasing spring 70 can cause the trigger 24 to move back to the initial position.

As indicated above, in an exemplary embodiment the device can also include an overload mechanism that is configured to prevent excess force being applied to the jaws by the closure assembly when thick tissue or other resistance is encountered. For example, when the device encounters resistance, the overload mechanism can be configured to allow the trigger to continue to pivot without causing further pivotal movement of the cam lever and thus without causing further distal movement of the sled to close the jaws. The overload mechanism instead can allow the force applied to actuate the trigger 24 to be transferred to the overload mechanism, thus preventing failure of the actuation mechanism. The overload mechanism 300 can have a predetermined threshold force that defines when the overload mechanism is activated.

Figure 5A:
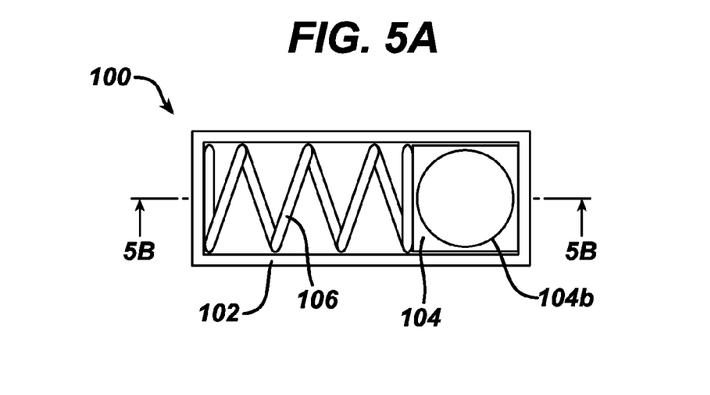
FIG. 5A is a side perspective view of one embodiment of an overload mechanism for use with the device of FIGS. 1A and 1B.
Figure 5B:
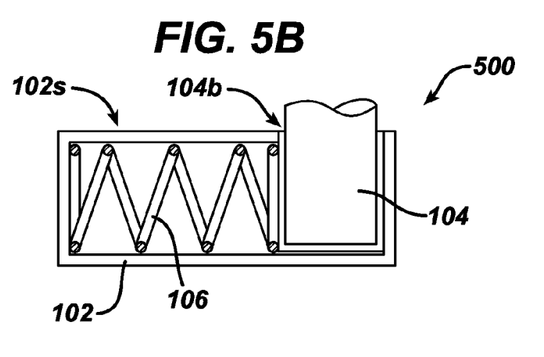
FIG. 5B is a top perspective view of the overload mechanism of FIG. 5A in an initial position.
Figure 5C:
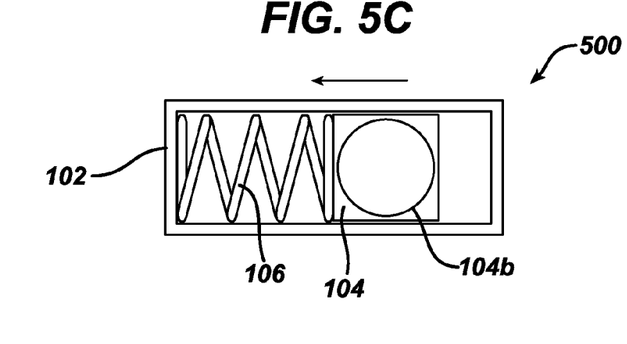
FIG. 5C is a top perspective view of the overload mechanism of FIG. 5A in an actuated position.

FIGS. 5A-5C illustrate one embodiment of an overload mechanism 100. In this embodiment, the overload mechanism 100 is in the form of a generally hollow rectangular six-sided housing 102 that is configured to be disposed within the handpiece. While the housing 102 is shown having a rectangular configuration, the housing 102 can have any shape or configuration. Moreover, the housing 102 itself can be eliminated and the handpiece 20 can be configured to seat the internal components of the overload mechanism 100. For example, the left and right shrouds of the handpiece 20 can include recesses formed therein that define a path of movement for the overload components. A person skilled in the art will appreciate that a variety of techniques can be used to couple the overload mechanism to handpiece. As shown in FIG. 5B, the housing 102 in the illustrated embodiment includes a sidewall 102s that has an open configuration. This allows the overload mechanism 100 to couple to the trigger pivot pin 24p, as will be discussed in more detail below. The entire sidewall of the housing 102 can be absent, or the sidewall can include a groove formed therein for receiving the trigger pivot pin 24p. In either instance, the opening preferably extends entirely along a length of the overload mechanism 100, between proximal and distal ends thereof. This will allow the trigger pivot pin 24p to slide axially in a proximal-distal direction relative to the overload housing 102.

The internal components of the overload mechanism 100 can have various configurations, but in the illustrated embodiment the overload mechanism 100 includes a carriage 104 and a biasing element 106. The carriage 104 can be slidably disposed within the overload housing 102 such that it can move between proximal and distal positions. The carriage 104 can further include a bore 104b formed therein that rotatably seats the trigger pivot pin 24p in a fixed position within the carriage 104. As a result, the trigger pivot pin 24p and the carriage 104 can slide as a unit between proximal and distal positions. The biasing element 106, e.g. a spring or other spring-like member, can be positioned within the housing 102 and can apply a biasing force to the carriage 104. In an exemplary embodiment, the biasing element 106 biases the carriage 104 to a proximal position, shown in FIGS. 5A and 5B. In this position, the trigger pivot pin 24p is maintained in the initial position in which the trigger 24 pivots about the trigger pivot axis $T_a$. The biasing element 106 can apply a predetermined force to the carriage 104 that corresponds to a threshold force required to activate the overload mechanism 100. In particular, the biasing element 106 will prevent movement of the carriage 104, and thus the trigger pivot pin 24p, until a force applied to the carriage 104 exceeds the predetermined threshold force of the biasing element 106. When the threshold force is exceeded, the overload mechanism 100 will be activated and the carriage 104 will be forced to slide within the housing 102 against the force of the biasing element 106, as shown in FIG. 5C. The carriage 104 will thus move in a distal direction, as indicated by the arrow shown in FIG. 5C, to compress the biasing element 106.

Figure 6A:
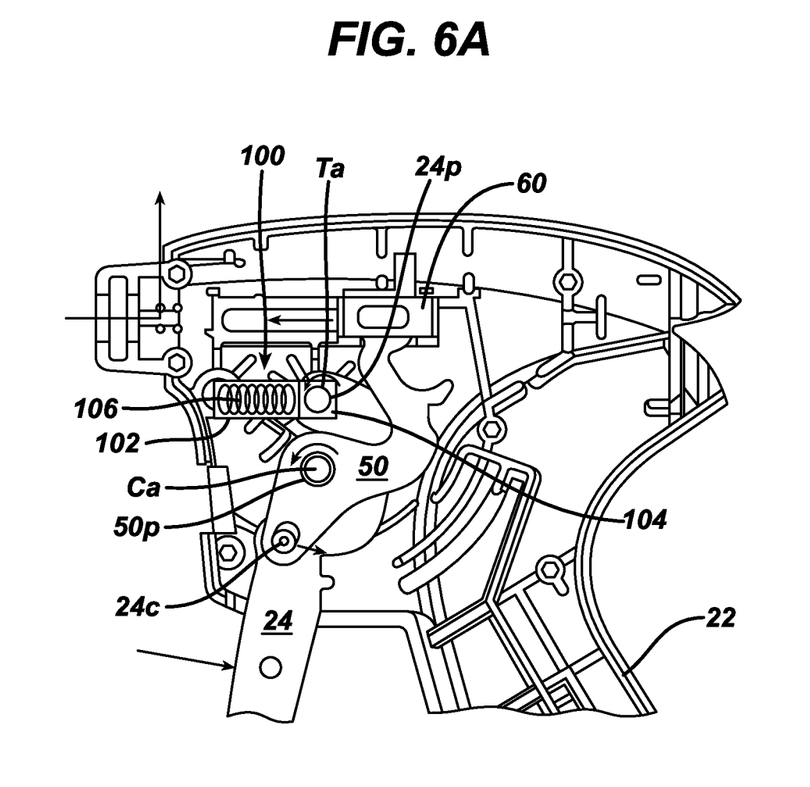
FIG. 6A is a side perspective view of the handle assembly of FIG. 1B with the overload mechanism of FIG. 5A disposed therein, showing the trigger and the overload mechanism both in an initial position.
Figure 6B:
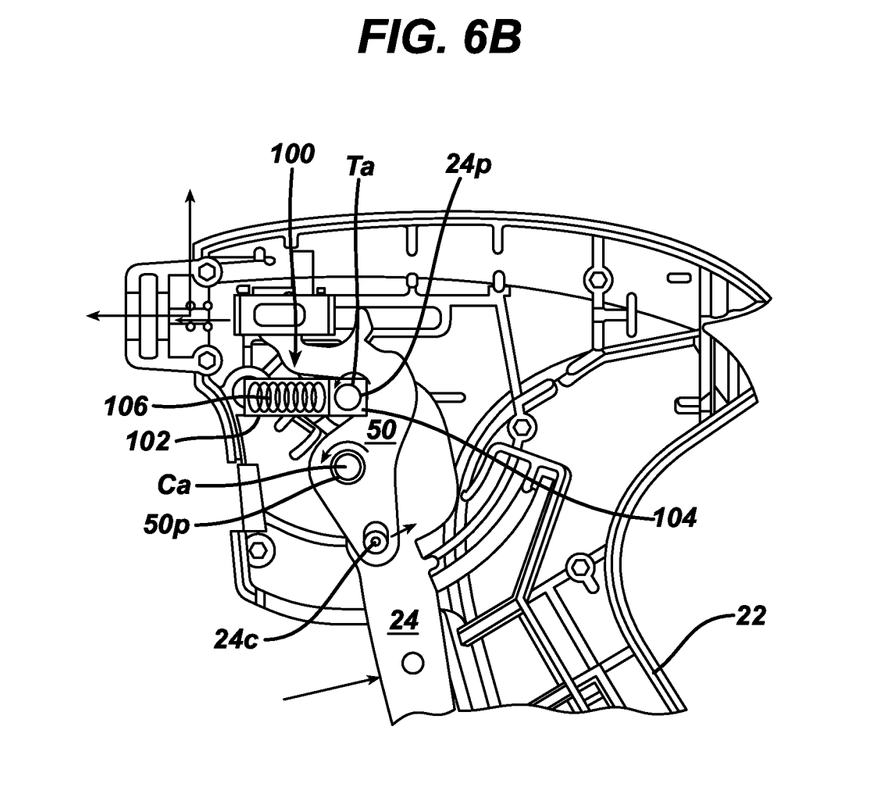
FIG. 6B is a side perspective view of the handle assembly and overload mechanism of FIG. 6A, showing the trigger moved toward the stationary handle to close the jaws, and showing the overload mechanism in the initial, unactuated position.
Figure 6C:
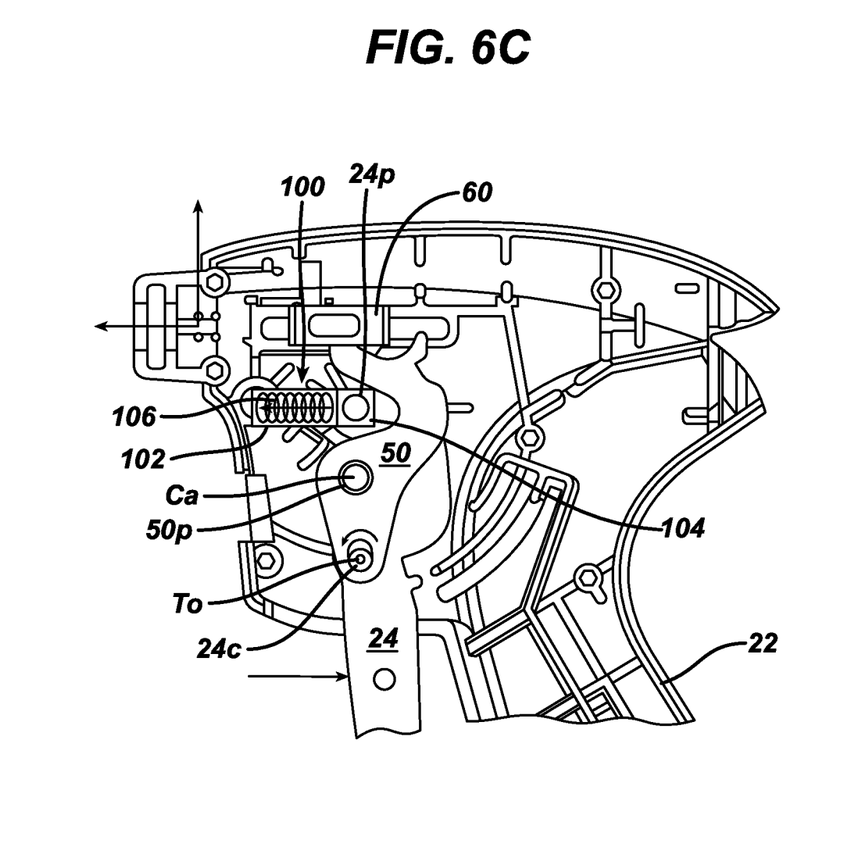
FIG. 6C is a side perspective view of the handle assembly and overload mechanism of FIG. 6A, showing the trigger moved toward the stationary handle to close the jaws, and showing the overload mechanism actuated under excessive load force.

FIGS. 6A-6C show the overload mechanism 100 disposed within the handpiece 20. As shown, the overload mechanism 100 is positioned such that the trigger pivot pin 24p extends into the carriage 104 in the overload mechanism 100, and the biasing element 106 is positioned distal of the carriage 104 and trigger pivot pin 24p to apply a proximally-directed biasing force to the carriage 104. In this position, as shown in FIG. 6A, the trigger 24 will pivot about the trigger pivot axis $T_a$ defined by the trigger pivot pin 24p.

Prior to actuation of the device, as shown in FIG. 6A, no force is applied to the trigger 24 and it is positioned in a spaced configuration with the stationary handle 22. The trigger 24 is biased to this initial position by the biasing spring 70 (shown in FIG. 1B). The cam lever 50 and the sled 60 of the actuation assembly are likewise in an initial position, in which the cam lever 50 has not yet rotated and the sled 60 is in a proximal most position. The overload mechanism 100 has not been engaged, and thus the carriage 104 and the trigger pivot pin 24p are disposed in a proximal-most position within the overload housing 102 as well.

When a normal force is applied to move the trigger 24 toward the stationary handle 22, the trigger 24 will pivot counterclockwise, as indicated by the arrow, about the trigger pivot pin 24p which defines the trigger pivot axis $T_a$. The trigger camming pin 24c on the trigger 24 will thus engage the camming bore 50b in the cam lever 50 to advance the sled 60 distally and thus close the jaws. For example, when a normal force is applied to the trigger 24, the trigger 24 overcomes the biasing force of the biasing spring 70 (FIG. 1B) that retains the trigger in the initial position. The lower portion 24l of the trigger 24 begins to travel in a proximal direction toward the stationary handle 22. As a result the cam lever 50 is forced to pivot counterclockwise, as indicated by the arrow, about the cam lever pivot axis $C_a$, thereby moving the sled 60 in a distal direction. The sled 60 can advance the elongated shaft 30 to cause the opposed jaws 42, 44 on the end effector to move from a spaced, open position to a closed, tissue-grasping position. The trigger 24 will continue to move through a full range of motion toward its final actuated position, shown in FIG. 6B, as long as the force required to actuate the trigger 24 and close the jaws does not exceed the predetermined threshold force of the biasing spring 106 in the overload mechanism 100. The overload mechanism 100 will thus remain disengaged and the carriage 104 containing the trigger pivot pin 24p will be maintained in its proximal-most position in the overload housing 102.

When an overload is encountered and the jaws are prevented from fully closing, e.g., due to thick tissue, the sled 60 will be prevented from moving to its distal-most position. Without the overload assembly 100, the sled 60 would in turn prevent further rotation of the cam lever 50, which would prevent further movement of the trigger 24 from the fully-open position (FIG. 6A) to the fully-closed position (FIG. 6B). If a user continued to apply an excess force to close the trigger 24, the various components of the device could malfunction and/or excessive pressure could be applied to the tissue by the jaws, potentially damaging the tissue. The overload mechanism 100 will thus allow movement of the trigger 24 to the fully closed position, while preventing further distal movement of the sled 60, and thus preventing malfunction of the device. In other words, the overload mechanism 100 will prevent a user from applying a force to the jaws that exceeds a predetermined threshold force, thereby preventing a user from damaging the device and/or the tissue engaged between the jaws.

FIG. 6C illustrates the device 10 when an overload force is encountered, e.g., when a force required to close the trigger 24 exceeds the threshold force set by the biasing spring 106 in the overload mechanism 100. Since the sled 60 is prevented from moving further distally, and the cam lever 50 is prevented from further pivotal movement about the cam lever pivot axis $C_a$. The overload mechanism 100 allows the trigger pivot pin 24p to move from its initial position, in which the trigger 24 pivots about the trigger pivot axis $T_a$, into an overload position, in which the trigger 24 pivots about an overload pivot axis $T_o$. In particular, the force applied to rotate the trigger 24 will exceed the threshold force of the biasing spring 106 in the overload mechanism 100, thereby causing the carriage 104 containing the trigger pivot pin 24 to slide distally, compressing the spring 106. Since the trigger pivot pin 24p is now allowed to move, the trigger pivot pin 24p no longer defines a fixed pivot point for the trigger 24 to rotate about. Thus, the trigger 24 in the overload state will no longer pivot about the trigger pivot axis $T_a$. Instead, the trigger 24 will pivot counterclockwise about the trigger camming pin 24c, which is held fixed and will thus define the new trigger overload pivot axis $T_o$. The trigger camming pin 24c is held stationary by the sled 60, which is prevented from further distal movement. Accordingly, when a force exceeding the threshold force is required to close the jaws, the overload mechanism 100 will activate and prevent the trigger 24 from causing further pivotal movement of the cam lever 50, thus preventing further distal movement of the sled 60 to further close the jaws. Since the trigger 24 is allowed to pivot about the trigger overload axis $T_o$, the trigger 24 can move to its final, fully engaged position adjacent to the stationary handle 22. In sum, when an overload is encountered, the trigger 24 will shift from a first state, in which the trigger pivots about the trigger pivot axis $T_a$, to an overload state, in which the trigger pivots about the trigger overload pivot axis $T_o$. The device will thus allow a user to fully close the trigger 24 without applying a force to the jaws that exceeds the threshold force as set by the overload mechanism 100. When the trigger 24 is released, the biasing element 106 in the overload mechanism 100 will move the carriage 104 back to the initial proximal position, and the biasing spring 70 in the hand piece will open the trigger 24, thereby resetting the device.

Figure 7:
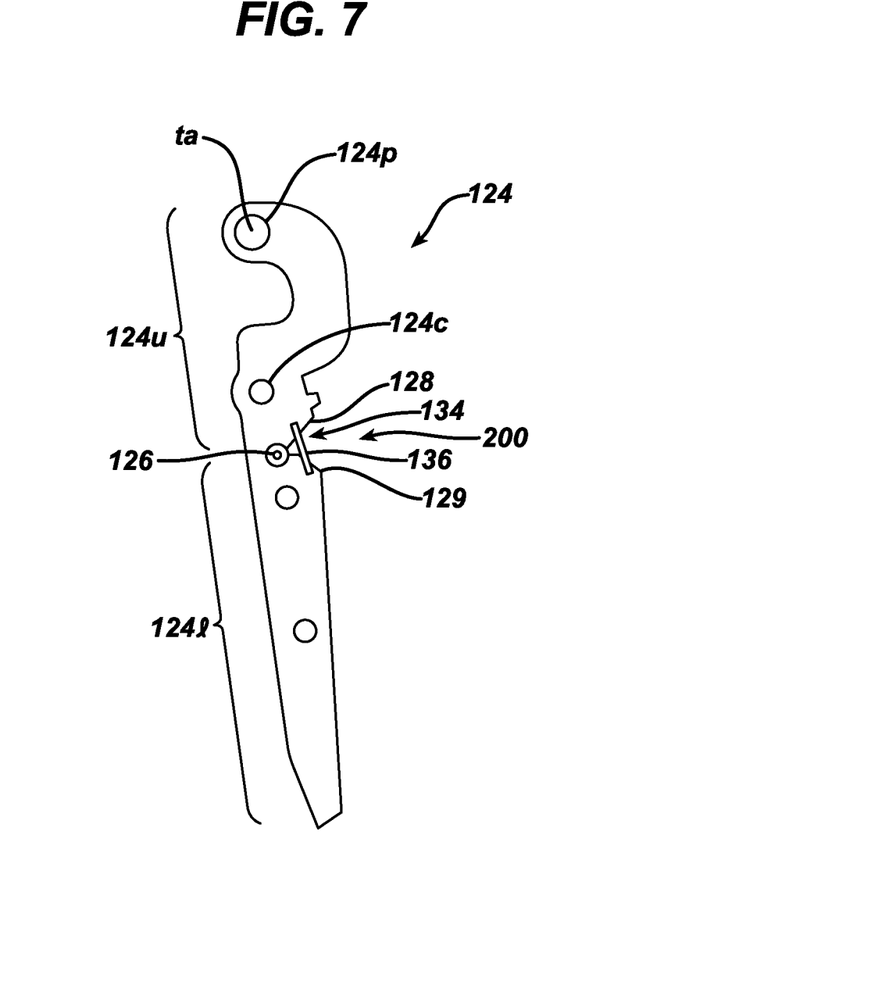
FIG. 7 is a side perspective view of another embodiment of an overload mechanism for use with the device of FIGS. 1A and 1B.

FIG. 7 depicts another embodiment of an overload mechanism 200 for preventing an excessive force from being applied the jaws. In this embodiment, the overload mechanism 200 is integral with the trigger 124. While not shown, the 124 trigger is configured to replace the trigger 24 of the device 10 shown in FIGS. 1A-1B. As shown, the trigger 124 includes an upper portion 124u and a lower portion 124l that are hingedly connected. The upper portion 124u is similar to the upper portion 24u of trigger 24, and can thus include all of the same features and functionality of the prior embodiment. In particular, the upper portion 124u includes a c-shaped configuration with a trigger pivot bore 124p, which can include a pin (not shown) for defining a trigger pivot axis to of the trigger 124, as well as a trigger camming bore 124c, which receives a pin that couples to the cam lever (not shown). While bores 124p, 124c are shown, pins can be disposed therein and/or integrally formed on the trigger 124. The lower portion 124l is configured to be positioned external to the handpiece 20 and to allow grasping by a user. While not shown, the lower portion 124l can have various features to facilitate gripping, including the same configuration as trigger 24.

As indicated above, the upper and lower portions 124u, 124l of the trigger 124 are coupled by a hinge. As shown, the hinge can be formed by a pivot joint 126 formed between the two portions, e.g., a pin and bore configuration to allow pivotal movement of the portions relative to one another. An angled surface 128, 129 is preferably formed on a proximal-facing surface of each of the upper and lower portions 124u, 124l, adjacent to the pivot joint 126. The angled surfaces 128, 129 define a recess 134 therebetween, and allow the upper and lower portions 124u, 124l to move toward one another to decrease a size of the recess 134. As further shown in FIG. 7, a biasing element 136, e.g., a leaf spring or other type spring, can be disposed within the recess 134 and can extend between the angled surfaces 128, 129. The biasing element 136 is configured to bias the upper and lower portions 124u, 124l to the initial configuration, as shown in FIG. 7. The biasing element 136 defines a predetermined threshold force that, similar to the aforementioned embodiment, prevents an excess force from being applied to the cam lever, the sled, and ultimately the jaws.

When the device is operating under heavy load conditions, and a force that exceeds the threshold force is required to move the trigger 124 to the fully closed position, adjacent to the stationary handle, the overload mechanism 200 will be activated. In particular, the biasing force of the biasing element 136 will be overcome, thus allowing the biasing element 136 to buckle, deform, or otherwise compress. As a result, the upper and lower portions 124u, 124l can pivot about the pivot joint 126, thereby moving toward one another to decrease a size of the recess 134 between the angled surfaces 128, 129. Such a configuration will allow the lower portion 124l of the trigger 124 to continue to move toward the stationary handle to the fully actuated position without causing further pivotal movement of the upper portion 124u of the trigger 124. As a result, since the upper portion 124u of the trigger 124 remains stationary, the upper portion 124u will not cause further pivotal movement of the cam lever and will thus not move the sled further distally to close the jaws. Accordingly, the overload mechanism 200 allows the trigger 124 to move to the fully closed position without further closing the jaws, thereby preventing an excess force from being applied to the jaws. When the trigger 124 is released, the biasing spring 136 of the overload mechanism 200 will return the trigger 124 to the initial configuration, shown in FIG. 7.

A person skilled in the art will appreciate that the overload mechanisms disclosed herein can be used in a variety of surgical devices to prevent overload of various actuation mechanisms. The present invention also has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a handle having an elongate shaft extending distally therefrom with opposed jaws coupled to a distal end thereof;
   a trigger coupled to the handle and movable between an open position and a closed position, the trigger being pivotally movable about a first pivot axis during a first range of motion from the open position toward the closed position to cause the opposed jaws of the end effector to move from an open position to a partially-closed position, and the trigger being pivotally movable about a second pivot axis during a second range of motion from a partially-closed position to the fully closed position and
   an overload mechanism disposed within the handle, wherein the overload mechanism is configured to maintain the opposed jaws in the partially closed position during movement of the trigger about the second pivot axis.

2. The device of claim 1, wherein the trigger includes a pin mounted thereon and coupled to the overload mechanism, the pin remaining stationary during movement of the trigger about the first pivot axis and the pin sliding within the overload mechanism during movement of the trigger about the second pivot axis.

3. The device of claim 1, wherein the overload mechanism includes a carriage that receives a pin on the trigger, and a biasing element that applies a proximal biasing force to the carriage, the pin causing distal movement of the carriage during movement of the trigger about the second pivot axis.

4. The device of claim 1, wherein the overload mechanism applies a biasing force to trigger to prevent movement of the trigger about the second pivot axis until a force to pivot the trigger exceeds a threshold force of the overload mechanism.

5. The device of claim 1, further comprising an actuation assembly disposed within the handle and the elongate shaft and coupled between the trigger and the opposed jaws, movement of the trigger about the first pivot axis being effective to advance the actuation assembly through the elongate shaft to cause the opposed jaws to move from the open position to the partially-closed position.

6. The device of claim 5, further comprising a cam lever coupled between the trigger and the actuation assembly, the trigger causing pivotal movement of the cam lever about a third pivot axis during movement of the trigger about the first pivot axis such that the cam lever applies a force to advance the actuation assembly through the elongate shaft.

7. A surgical device, comprising:
a handle housing having a trigger coupled thereto;
an elongate shaft extending distally from the handle housing and having an end effector with opposed jaws coupled to a distal end thereof;
an actuation assembly extending through the handle housing and the elongate shaft and configured to actuate the end effector;
a cam lever disposed within the handle housing and coupled between the trigger and the actuation assembly such that movement of the trigger about a first axis to a first position causes the cam lever to pivot which in turn advances the actuation assembly to actuate the end effector; and
an overload mechanism disposed within the handle housing and configured to apply a proximal biasing force to the trigger to maintain the trigger in the first position in which movement of the trigger about the first axis is effective to cause the cam lever to pivot and thereby advance the actuation assembly to actuate the end effector, and wherein, when a force applied to the trigger exceeds a predetermined threshold force of the overload mechanism, the overload mechanism allows the trigger to pivot about a second axis to move to a second position in which the trigger can continue to pivot without causing further pivotal movement of the cam lever.

8. The device of claim 7, wherein the actuation assembly is effective to close the opposed jaws of the end effector.

9. The device of claim 7, wherein the overload mechanism includes a biasing element that applies the biasing force to the handle.

10. The device of claim 7, wherein the overload mechanism includes a housing having a biasing element that biases a carriage disposed within the housing, the trigger having a pin that is received within the carriage.

11. The device of claim 10, wherein the biasing element biases the carriage in a proximal direction, and wherein movement of the trigger about the second pivot axis causes the carriage to move distally within the housing.

12. The device of claim 7, wherein the overload mechanism is positioned distal of the cam lever.

13. The device of claim 7, further comprising a pin coupled between the trigger and the cam lever such that rotation of the trigger causes rotation of the cam lever.

14. The device of claim 7, wherein the cam lever is disposed about a third pivot axis, and the trigger pivots in the first position to cause the cam lever to pivot about the third pivot axis, and the cam lever remains stationary about the third pivot axis during movement of the trigger in the second position.

15. The device of claim 7, wherein the trigger includes a pin that applies a force to the cam lever to cause pivotal movement the cam lever when the trigger moves in the first position.

16. A method of operating a surgical device, comprising:
actuating a trigger movably coupled to a handle housing to cause the trigger to pivot about a first pivot axis and thereby advance an actuation assembly extending through an elongated shaft extending distally from the handle housing, advancement of the actuation assembly causing opposed jaws at a distal end of the elongate shaft to move from an open position to a closed position, wherein an overload mechanism disposed within the handle housing allows the trigger to pivot about a second pivot axis when a force applied to the trigger to close the opposed jaws exceeds a predetermined level without further advancing the actuation assembly to close the opposed jaws.

17. The method of claim 16, wherein movement of the trigger about the second pivot axis causes a pin on the trigger to slide distally within the overload mechanism and to overcome a biasing force of a biasing element disposed within the overload mechanism.

18. The method of claim 16, wherein movement of the trigger about the first pivot axis causes pivotal movement of a cam lever disposed within the housing, the cam lever causing advancement of the actuation assembly, and wherein the cam lever remains stationary during movement of the trigger about the second pivot axis.

* * * * *